(12) United States Patent
Hollmann et al.

(10) Patent No.: US 9,194,871 B2
(45) Date of Patent: *Nov. 24, 2015

(54) MONOCLONAL ANTIBODIES WITH SPECIFICITY FOR FETAL ERYTHROID CELLS

(71) Applicant: KellBenx Inc., Great River, NY (US)

(72) Inventors: Christiane Hollmann, Wedemark (DE); Silke Zimmermann, Hannover (DE); Stefan Stachelhaus, Wedemark (DE); Winfried Albert, Penzberg (DE)

(73) Assignee: KellBenx Inc., Great River, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,027

(22) Filed: Sep. 16, 2013

(65) Prior Publication Data

US 2014/0154704 A1   Jun. 5, 2014

Related U.S. Application Data

(60) Continuation of application No. 12/979,535, filed on Dec. 28, 2010, now Pat. No. 8,536,312, which is a division of application No. 10/599,512, filed as application No. PCT/EP2005/003371 on Mar. 31, 2005, now Pat. No. 7,858,757.

(30) Foreign Application Priority Data

Mar. 31, 2004  (EP) ..................... 04007811

(51) Int. Cl.
*G01N 33/80* (2006.01)
*C07K 16/28* (2006.01)
(Continued)

(52) U.S. Cl.
CPC .......... *G01N 33/56966* (2013.01); *C07K 16/28* (2013.01); *G01N 33/5094* (2013.01); *G01N 33/577* (2013.01); *G01N 33/80* (2013.01);
(Continued)

(58) Field of Classification Search
CPC ................... G01N 33/56966; G01N 33/5094; G01N 33/577; G01N 33/80; C07K 16/28
USPC ................... 435/7.2, 7.25, 40.5, 343, 287.2; 436/520, 523, 526, 547, 548, 63, 436/161.175, 177, 811; 530/380, 386, 530/388.1, 388.2, 388.22, 388.23
See application file for complete search history.

(56) References Cited

U.S. PATENT DOCUMENTS 7,858,757 B2 * 12/2010 Hollmann et al. ....... 530/388.22
2003/0180762 A1 * 9/2003 Tuma et al. ................. 435/6

FOREIGN PATENT DOCUMENTS

WO    WO 02/101387    12/2002

OTHER PUBLICATIONS

Alvarez et al. Development, Characterization, and Use of Monoclonal Antibodies Made to Antigens Expressed on the Surface of Fetal Nucleated Red Blood Cells, Clinical Chemistry 45 (9):1614-1620, (1999).*

(Continued)

*Primary Examiner* — Gail R Gabel
(74) *Attorney, Agent, or Firm* — Biospark Intellectual Property Law (57) ABSTRACT

The present invention concerns a monoclonal antibody and corresponding hybridoma cells and antigens suitable for isolating fetal cells from maternal blood. The inventive monoclonal antibody reacts with a surface antigen present on fetal red blood cells including their nucleated precursor cells, but not with surface antigens on adult erythroid cell.

16 Claims, 4 Drawing Sheets

(51) Int. Cl.
G01N 33/577 (2006.01)
G01N 33/569 (2006.01)
G01N 33/50 (2006.01)

(52) U.S. Cl.
CPC .. Y10T436/25125 (2015.01); Y10T 436/25375 (2015.01)

(56) References Cited

OTHER PUBLICATIONS

Bianchi et al. Erythroid-Specific Antibodies Enhance Detection of Fetal Nucleated Erythrocytes in Maternal Blood, Prenatal Diagnosis, 13: 293-300 (1993).*

Sitar et al., 2005, "The use of non-physiological conditions to isolate fetal cells from maternal blood," *Experimental Cell Research* 302:153-161, 2005.

Bianchi et al., "Fetal Cells in the maternal circulation: feasibility for prenatal diagnosis," *Br. J. Haematology,* 105:574-583, 1999.

Blanchard et al., "Caractérisation d'anticorps monoclonaux murins dirigés contre les erythrocytes foetaux," *Revue francaise de transfusion et d'hemobiologie,* 35:239-254, 1992. Abstract.

Huie et al., "Antibodies to human fetal erythroid cells from a non immune phage antibody library," *Proc. Natl. Acad. Sci. USA,* 98:2682-2687, 2001.

Office Communication issued in U.S. Appl. No. 10/599,512, dated Aug. 7, 2009.

Office Communication issued in U.S. Appl. No. 10/599,512, dated Feb. 1, 2010.

Reid et al., *The Blood Group Antigen Factsbook,* ($2^{nd}$ Ed.) Elsevier Academic Press, London, 271-488, 2004.

Zimmerman, Silke, *Development of a fetal specific antibody to characterize fetal erythroid cells,* University of Hannover, 2004.

Zimmerman, Silke et al., "Unique monoclonal antibodies specifically bind surface structures on human fetal erythroid blood cells," *Experimental Cell Research,* 319:2700-2707, 2013.

English language translation of Blanchard et al., 1992, "Caractérisation d'anticorps monoclonaux murins dirigés contre les erythrocytes foetaux," *Revue française de transfusion et d'hémobiologie* 35:239-254.

* cited by examiner

MONOCLONAL ANTIBODIES WITH SPECIFICITY FOR FETAL ERYTHROID CELLS

This application is a continuation of, and claims priority to, U.S. patent application Ser. No. 12/979,535 filed Dec. 28, 2010, issued as U.S. Pat. No. 8,536,312, which is a divisional application of U.S. patent application Ser. No. 10/599,512, filed Sep. 29, 2006 and issued as U.S. Pat. No. 7,858,757 on Dec. 28, 2010, which is a national phase application under 35 U.S.C. §371 of International Application No. PCT/EP2005/003371 filed Mar. 31, 2005, which claims priority to European Patent Application No. 04007811.5 filed Mar. 31, 2004. The entire text of the above-referenced disclosures is specifically incorporated herein by reference without disclaimer.

INTRODUCTION

Social developments led to an increase of prenatal investigations. Amniocentesis or less frequently sampling of chorionic villi is performed in every tenth pregnancy for the prenatal analysis of, e.g. trisomy 21. The risk for a chromosomal defect increases with the age of the mother. This is why amniocentesis is performed in more than 50% of pregnant women aged 35 years or older. However, most children with chromosomal or genetic defects are still born by women under the age of 35, if the total number is taken into account. The probability for a trisomy 21 is 0.3% in fetuses of women aged 35 years and older. This has to be seen in the context of a 0.5% risk to induce an abortion by the amniocentesis procedure. From these numbers it is obvious that there is a great need for an alternative diagnostic procedure which yields the same results without bearing a risk for the unborn. One approach could be the isolation of fetal cells from maternal blood. This would eliminate risks for the fetus.

It was estimated that one fetal cell can be found in $10^5$ to $10^7$ maternal nucleated blood cells. Further investigations have shown, that in the presence of chromosomal aberrations more fetal cells can be detected in the maternal circulation. This raises the chance to detect an aneuploid fetus by non-invasive procedures.

Three different types of fetal cells have been identified in maternal blood: lymphocytes, trophoblasts and nucleated red blood cells (NRBCs). Fetal lymphocytes have been detected still one to 5 years after childbirth. This longevity may interfere with the accurate diagnosis in following pregnancies.

Trophoblasts are attractive targets because they can be easily identified by their morphology. However, they can not be easily used for diagnostic purposes, because as placental cells they might differ from cells of the fetus: in about 1% of diagnosed chromosomal aberrations in trophoblasts the fetus turned out to be healthy.

Fetal nucleated red blood cells (NRBCs) appear early in the maternal circulation, however do not persist after birth. Since they have a nucleus they are preferred candidates for chromosomal analysis. However, up to now they can not be distinguished easily and unambiguously from other blood cells. They are identified through a marker profile, which is characteristic for erythroid precursor cells and which is different from other blood cell subpopulations. Blood cells are extensively characterized by so-called clusters of differentiation (CD) markers as defined at the $7^{th}$ Workshop and Conference on Human Leukocyte Differentiation Antigens (Harrogate 2000). Immature erythroid cells express CD71 and they lack CD45 which is expressed on leukocytes. This knowledge can be used to distinguish erythroid precursor cells from other mononuclear cells.

In order to isolate and identify fetal cells (1 amongst $10^5$ to $10^7$ maternal nucleated cells) most stringent criteria have to be met. There is no cell surface marker available yet which is exclusively expressed on fetal NRBCs. For the enrichment of fetal cells usually immunomagnetic or flow cytometric cell separation techniques are used either alone or in combination. The results of the chromosomal or genetic analysis of the isolated cells have been compared with the results obtained with amniotic cells. Many investigations have shown the technical feasibility of the non-invasive approach with large cohorts.

However, the existing procedures are still not suitable for routine diagnosis. It has to be assured that the cells under investigation are unambiguously fetal cells. The identification of fetal NRBCs can only be achieved by the recognition of a marker, which is preferentially expressed on fetal erythroid cells or which is expressed or localized in a way that is specific for fetal cells within the blood.

The lack of markers, which specifically identify fetal cells is the crucial obstacle for the development of a reliable non-invasive prenatal diagnostic.

The objective of this invention is the generation of antibodies, which allow the discrimination between fetal and adult erythroid cells and the unambiguous identification of fetal cells. Fetal cells recognized by these antibodies preferably should possess at least in part an intact cell nucleus, express the CD71 antigen and should miss the CD45 antigen in line with previously published results.

Further, the object of the invention is the generation of monoclonal antibodies, which react specifically with fetal cells as well as a hybridoma cell line, which produces such antibodies. This object is solved by the antibody according to embodiment 1, 7 or 10, the antigen according to claim 9 and the hybridoma cell according to embodiment 4 or 5. Further improvements of the antibodies, the hybridoma cell and the antigen are given in the embodiments 2-6, 8, and 11-16.

1. Monoclonal antibody reacting with a surface antigen present on fetal red blood cells including their nucleated precursor cells, but not with surface antigens on adult erythroid cells.

2. Antibody according to embodiment 1, characterized in that it reacts with most or all fetal erythroid cells, which express the CD71 antigen but are negative for CD45 antigen expression.

3. Antibody according to embodiment 1 or 2, characterized in that it reacts with fetal erythroid cells but not with the CD71 antigen.

4. Hybridoma cell producing monoclonal antibodies according to one of the preceding embodiments.

5. Hybridoma cell as deposited under accession number DSM ACC 2666 on Jul. 13, 2004 at the Deutsche Sammlung von Mikroorganismen and Zellkulturen GmbH in Braunschweig, Germany.

6. Hybridoma cell according to embodiments 4 and 5.

7. Antibody expressed by the hybridoma cell according to one of embodiments 4 to 6.

8. Antibody according to embodiment 7 and one of embodiments 1 to 3.

9. Surface antigen on fetal red blood cells recognized by a monoclonal antibody as characterized in one of embodiments 1 to 3 and 7 to 8.

10. Antibody characterized in that it recognizes or binds specifically to a surface antigen according to embodiment 9.

11. Use of a monoclonal antibody according to one of embodiments 1 to 3, 7, 8 or 10 for the detection and identification of fetal cells in a sample.

12. Use according to the preceding embodiment for the detection and identification of fetal cells in a sample of maternal blood.

13. Method for detection or identification of fetal cells in a sample, characterized by labeling said fetal cells by an antibody according to one of embodiments 1 to 3, 7, 8, or 10.

14. Method according to the preceding embodiment, characterized in that the sample is maternal blood or a sample of maternal blood.

15. Use of a method according to embodiments 13 or 14 for the detection of chromosomal and/or genetic aberrations, defects and/or variants in the fetal cells detected and identified by a method according to embodiment 13 to 14, characterized in that said fetal cells are subsequent to the detection and identification analyzed for a chromosomal and/or genetic aberration, defects and/or variant.

16. Use or method according to one of embodiments 11 to 15, characterized in that cells binding the monoclonal antibody are separated by flow cytometry, solid phase separation, immunomagnetic bead separation, panning on plastic surfaces, or the like.

For the purpose of the present invention 5 mice have been immunized with isolated erythroid cells from cord blood (CD71+, CD45−), which carried the "i" antigen as defined by the autoantibody described in DE 100 35 433 A1. The immunization with these cells opens the possibility that besides antibodies against the "i" antigen also antibodies with specificities against new markers could be generated, which could be used to identify erythroid precursor cells. The spleen cells of the immunized mice were fused with a myeloma cell line to produce hybridomas according to standard procedures (Schetters H, Production of Monoclonal Antibodies, in: Methods of Immunological Analysis, Masseyeff R F, Albert W H and Staines N A (Eds.) Vol. 2, Ch. 4.3, 230-245, VCH Weinheim, 1993).

DESIGN AND METHODS IN DETAIL

In detail, mice were immunized with flow sorted human cord blood cells (CD71+, antigen-i+, CD19− and CD45−). Hybridoma supernatants were screened on pooled mononuclear cord blood cells, whereas the corresponding amount of erythroid precursors was determined by cytochemical staining of blood smears. For the hybridoma screening a six-parameter flow cytometric analysis (four colours, forward and side scatter) was set up for the simultaneous identification of erythroid precursor cells, leukocytes, enucleated erythrocytes and for antibodies reacting specifically with fetal cells. Furthermore, immunohistochemical analyses have been performed with fetal blood smears and fetal liver sections from the $6^{th}$ up to $38^{th}$ week of gestation as well as with adult blood, normal adult bone marrow and adult erythrocytes as controls.

Results:

A clone (accession number DSM ACC 2666 at the Deutsche Sammlung von Mikroorganismen und Zellkulturen GmbH (DSMZ)) with specificity for a surface antigen exclusively expressed on fetal erythroid cells has been identified. The new antibody showed unaltered binding to erythroid cells from fetal blood of early times of gestation ($6^{th}$ week) up to childbirth. Moreover, detailed examinations showed no surface reactivity with adult erythrocytes, erythroblasts or lymphatic and myeloid cells. This antibody did not react with cells of fetal haemolymphatic organs.

CONCLUSIONS

The investigation showed that the new monoclonal antibody binds specifically fetal erythroid cells and thus can differentiate between fetal and adult red blood cells. Because of the expression of this fetal antigen in early stages of gestation a noninvasive prenatal diagnostic may be feasible. This antibody can be applied for different enrichment techniques and/or for the identification of fetal erythroid cells.

Detailed Analysis of Hybridoma Cells

Screening for Hybridomas Producing Antibodies Reacting Specifically with Fetal NRBCs Since several thousand antibody producing hybridomas have to be screened to find a suitable clone a procedure has been set up permitting a high through-put whilst maintaining the required specificity. A six-parameter analysis (4 fluorescence channels, forward and side scatter) has been established, which enabled the simultaneous identification of erythroid precursor cells, the differentiation of leukocytes from enucleated erythrocytes and the identification of new antibodies in a single step. The analysed cells have been stained with a nucleic acid dye (LDS751, Molecular Probes, cat#7595) and have been incubated with antibodies of the cloned hybridomas. These antibodies were subjected to a reaction with an antibody directed against them, which was labeled with a fluorescent dye (FITC) (Goat anti mouse IgG (H+L)-FITC, Caltag Laboratories, cat# M35001). In later experiments for antibody characterization the antibodies have been labeled directly with FITC.

Figure 1:
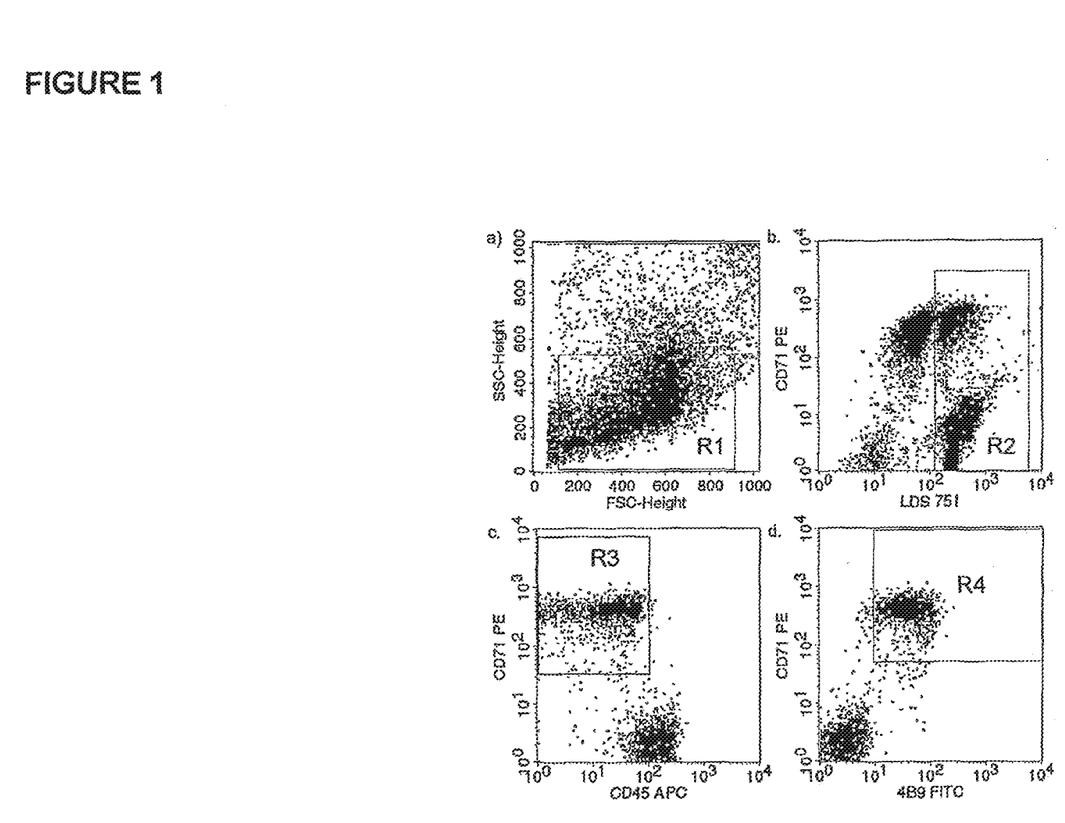
FIG. 1A is a diagram of the light scatter properties of erythroid precursor cells.
FIG. 1B is a diagram of fluorescence properties of the cells in region R1 and labeled with CD71-antibody and dye LDS751 labeling all nuclei.
FIG. 1C is a diagram of fluorescence properties of cells in region R2 incubated with CD71 antibodies.
FIG. 1D is a diagram of fluorescence properties of the cells in region R2.

The identification of the erythroid precursor cells is possible due to their light scatter characteristics and by their binding of phycoerythrin labeled CD71 specific antibodies (CD71 PE, Diatec, cat#3212). Leukocytes could be discerned by their binding to allophycocyanin labeled CD45 specific antibodies (CD45 APC, BD Pharmingen, cat#555485). Nucleated and enucleated erythroid cells can be distinguished by their binding or absence of binding of the nucleic acid dye. With this procedure it is possible to identify antibodies binding to the intended target cells, i.e. fetal NRBCs, without cross-reaction towards adult erythrocytes or leukocytes (FIG. 1).

Figure 2:
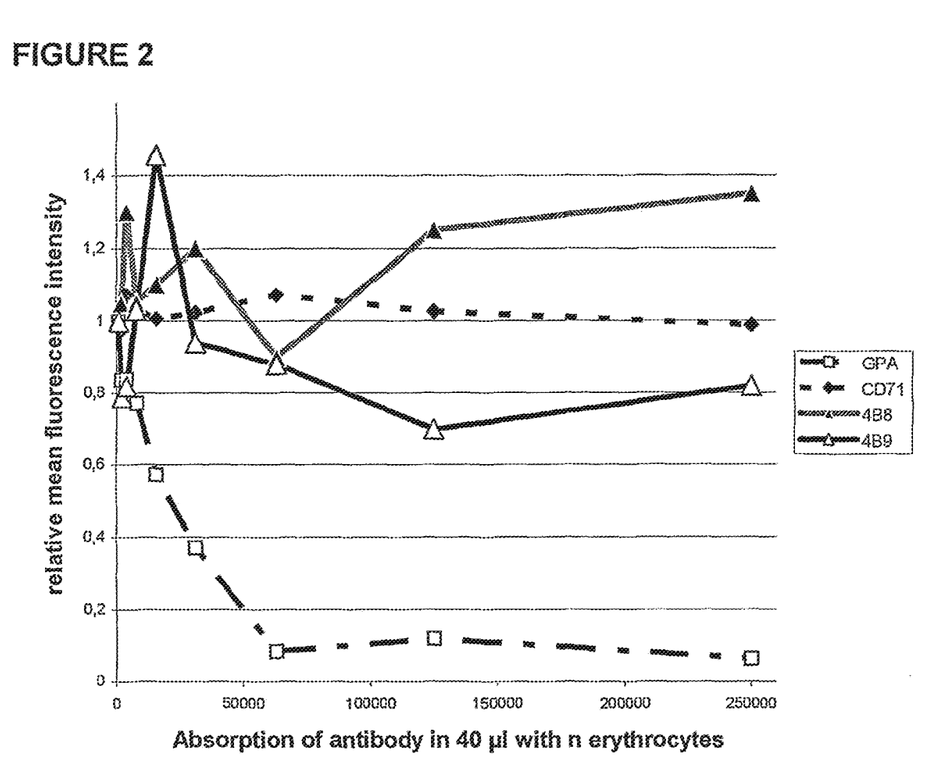
FIG. 2 is a graph showing the absorption of monoclonal antibodies 4B8 and 4B9 with adult erythrocytes, followed by the determination of their binding capability on cord blood cells.
Figure 3:
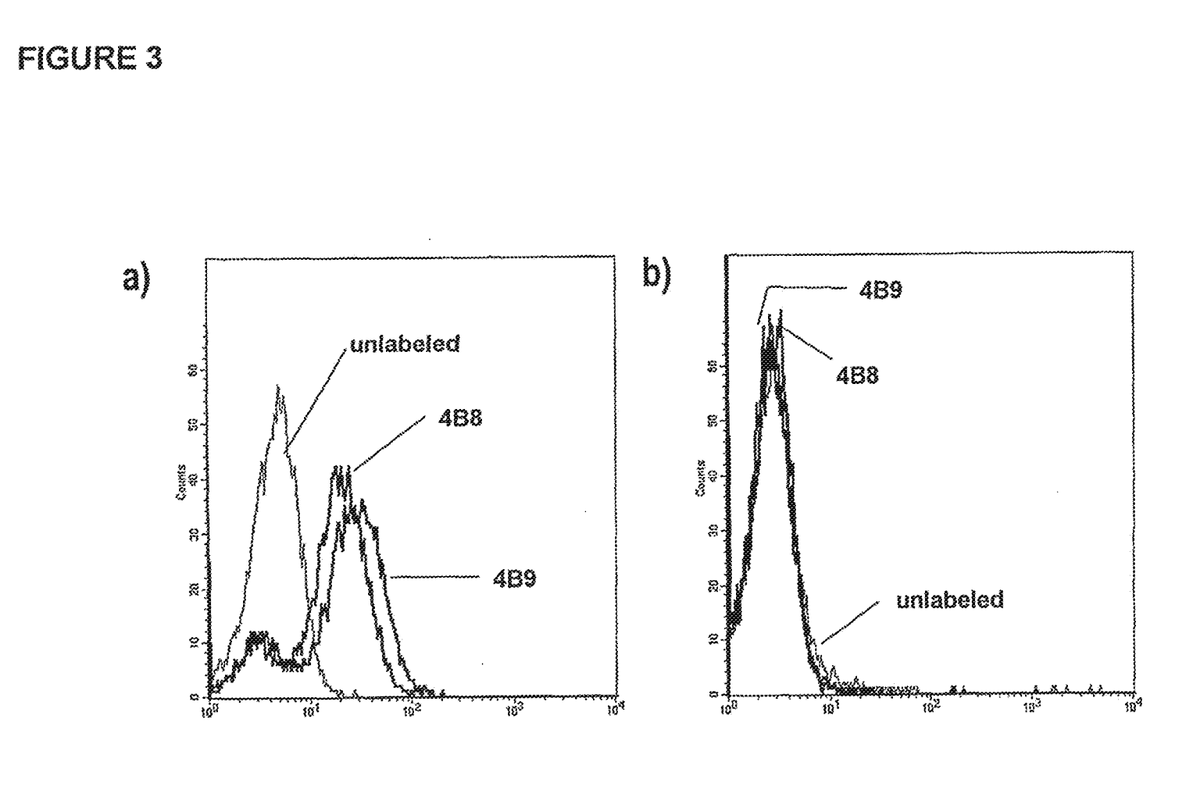
FIG. 3A is histogram showing unstained, negative cord blood cells marked as "unlabeled" and cord blood cells incubated with labeled antibodies 4B8 and 4B9.
FIG. 3B is a histogram of the adult blood cells showing the same fluorescence intensity (x-axes), whether they are incubated as antibodies, 4B8, 4B9, or with no antibodies.

Exclusion of Antibodies Reacting with Antigens on Adult Erythrocytes Including Common Blood Group Antigens Blood group antigens can be found on adult erythrocytes and their precursors in large amounts. Therefore, they might induce a major immune response when used as antigens. Antibodies against these blood group antigens are not suitable for the identification of fetal cells. In order to exclude antibodies binding to antigens on adult erythrocytes including blood group antigens, their binding specificity towards fetal cells is investigated after absorption on erythrocytes. Erythrocyte with the blood group AB Rh+ have been harvested and stabilized with a reagent supplied by Meridian Diagnostics Europe, Bad Homburg. The antibodies under investigation have been incubated with increasing numbers of erythrocytes and tested before and afterwards for their binding activity for target cells. Reactivity of antibodies towards blood group antigens was thought to be absent, when the intensity of the binding to CD71+, CD45− nucleated erythroid precursor cells was unchanged after the incubation with the erythrocytes (FIG. 2). Antibodies selected that way must not react with adult blood cells to enable the correct identification of fetal erythroid precursor cells (FIG. 3).

Specificity Testing of a Selected Monoclonal Antibody

Hybridoma clone producing a monoclonal antibody of the IgM isotype showing the required binding characteristics in the screening procedure could be identified. It has the designation 4B9 and was deposited by the applicant of the present patent or patent application on Jul. 13, 2004 at the Deutsche Sammlung von Mikroorganismen and Zellkulturen GmbH (DSMZ, Braunschweig) under the accession number DSM ACC 2666. A second antibody 4B8 recognizing the same epitope is mentioned in FIGS. 2 and 3.

Fetal and adult erythroblasts strongly and specifically express glycophorin-A and, therefore, can be identified through this marker protein. The binding of the monoclonal antibody to these cells was visualized by an immunofluorescence double stain.

Protocol for Immunofluorescence Stain
1 Fix cytospins or frozen tissue sections in acetone for 10 min
2 Dry for 5 min
3 Apply monoclonal antibody against glycophorin-A, DAKO M0819 diluted 1:100 in phosphate buffered saline (PBS) containing 1% bovine serum albumin (BSA) for 60 min
4 Rinse with PBS
5 Apply goat anti-mouse antibody F(ab) fragment, Alexa Fluor 488 (Molecular Probes A-21044), green, diluted 1:100 in PBS for 60 min
6 Rinse with PBS
7 Apply monoclonal antibody 4B9 (hybridoma supernatant) for 60 min
8 Rinse with PBS
9 Apply goat anti-mouse IgM, Alexa Fluor 594 (Molecular Probes A-21044), red, for 60 min
10 Rinse with PBS
11 Stain cell nuclei with DAPI (Molecular Probes), blue, diluted 1:300 in PBS for 3 min
12 Rinse with PBS
13 Cover with fluorescence medium (S3023, DA-KO)
14 Visualize with "Universalmikroskop Axioplan", Carl Zeiss, using filter sets 02, 10 and 15 and photograph with a digital camera system, e.g. Visitron Systems GmbH
PBS: 8 g NaCl, 1.3 g Na HPO$_4$, 4 g NaH PO$_4$ in 1 l H$_2$O, pH 7.4

An immunoenzymatic method has also been used:

Protocol for Alkaline Phosphatase Anti-Alkaline Phosphatase (APAAP) Stain
1 Fix cytospins or frozen tissue slices in acetone for 10 min
2 Dry for 5 min
3 Incubate with monoclonal antibody 4B9 (hybridoma supernatant) for 30 min
4 Rinse with Tris buffered saline (TBS)
5 Incubate with APAAP complex (D0651, DAKO), diluted 1:25 in TBS/HS (inactivated human serum) for 30 min
6 Rinse with TBS
7 Repeat steps 5-7 twice for 10 min each
8 Rinse with TBS
9 Develop slides with substrate
   i. Prepare solution A: Mix 18 ml 0.2 mol/l 2-amino-2methyl-1,3-propandiol with 50 ml 0.05 mol/l Tris buffer, pH 9.7 and 600 mg NaCl. Add 28 mg levamisol.
   ii. Prepare solution B: Dissolve 35 mg naphthol AS-biphosphate in 0.42 ml N,N-dimethylformamide.
   iii. Prepare solution C: Mix 0.14 ml 5% New Fuchsin with 0.35 freshly prepared 4% sodium nitrite. Stir for 60 sec.
   iv. Mix solution A with solution B, then add solution C. Adjust the pH to 8.7. Mix, filter and apply to slides.
   v. Incubate for 10-20 min at room temperature.
   vi. Rinse with tap water.
   vii. Counter stain with Meyer's acid Haemalaun for 5 min.
   viii. "Blue" in tap water for 10 min and cover with Kaiser's glycerol gelatine.
TBS (Tris buffered saline): Dissolve 43.33 g NaCl and 39.40 g Tris-HCl in 5 l H$_2$O dest. Adjust pH to 7.4 with NaOH.
TBS/HS: 9 parts TBS+1 part inactivated human serum
Negative controls: monoclonal antibody of identical isotype or murine hyper-immune serum.

Exclusion of Antibodies Reacting with CD71

Antibodies generated with the immunization strategy used may be directed against CD71. To exclude these antibodies, analyses were performed that show whether CD71-antibodies compete for the same binding site. Biotinylated antibody 4B8 was preincubated with mononuclear cells from cord blood. Then unlabeled CD71-specific antibody (Anti-CD71, Clone DF1513, DPC Biermann, Bad Nauheim, Germany) was added. After streptavidin-DTAF-labeling it was analyzed by flow cytometry whether CD71-antibodies had replaced the antibody 4B8. As a positive control sample for this competition experiment, unlabeled antibody 4B8 was added instead of CD71. These analyses showed that antibodies 4B8 and CD71 do not compete for the same epitope whereas the addition of unlabeled antibody 4B8 had diminished the signal.

Results

Figure 4:
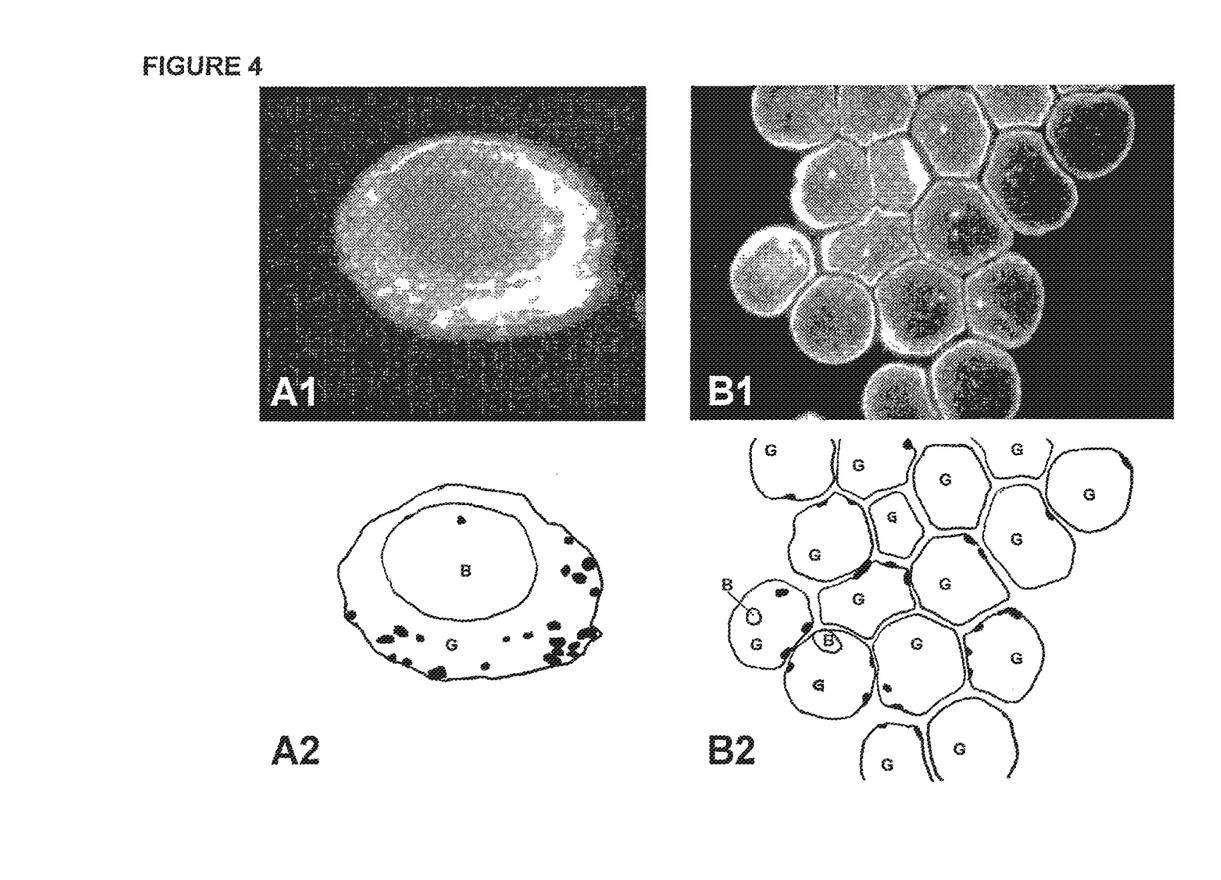
FIGS. 4A-B shows the immunofluorescent and immunoenzymatic analyses of fetal blood cells.

The 4B9-reactive antigen was expressed on the surface of fetal erythroblasts. This could be demonstrated with fetal cells from the 6. up to the 38th week of gestation. In FIG. 4 the antibody 4B9 recognised all glycophorin-A positive fetal erythroblasts.

Erythroblasts in normal adult bone marrow were negative for 4B9. In contrast, all erythropoietic cells were positive for glycophorin-A. Only in 1 of 32 cases a intracellular granular expression in the cytoplasm of early basophile erythroblasts was seen.

The 4B9 reactive antigen was not found on adult and fetal liver hepatocytes. Kupffer cells, macrophages, endothelial and sinusoidal cells were also negative.

A detailed analysis of haemolymphatic cells in adults showed the absence of reactivity in lymphatic and myeloic cells.

All haemolymphatic organs of the fetus were negative. This applies for lymphatic as well as myeloic cells.

TABLE 1

Detailed results of the reactivity of the monoclonal antibody 4B9

| Cell or tissue | Adult (n positive/n samples) | Fetal (n positive/n samples) |
|---|---|---|
| Granulopoiesis | | |

TABLE 1-continued

Detailed results of the reactivity of the monoclonal antibody 4B9

| Cell or tissue | Adult | Fetal |
|---|---|---|
| | (n positive/n samples) | |
| Neutrophils | | |
| Segmented | 0/8 | 0/14 |
| Rodforms | 0/8 | 0/14 |
| Metamyelocytes | 0/8 | 0/14 |
| Myelocytes | 0/8 | 0/14 |
| Promyelocytes | 0/8 | 0/14 |
| Eosinophils | | |
| Rodforms | 0/8 | 0/14 |
| Metamyelocytes | 0/8 | 0/14 |
| Myelocytes | 0/8 | 0/14 |
| Promyelocytes | 0/8 | 0/14 |
| Basophils | 0/8 | 0/14 |
| Monocytes | | |
| Mature monocytes | 0/8 | 0/14 |
| Promonocytes | 0/8 | 0/14 |
| Myelocyte | 0/8 | 0/14 |
| Macrophages | 0/8 | 0/14 |
| Thrombocytopoieses | | |
| Platelets | 0/8 | 0/14 |
| Megakaryocytes | 0/8 | 0/14 |
| Megakaryoblasts | 0/8 | 0/14 |
| Erythrocytopoiesis | | |
| Erythrocytes | 0/8 | 14/14 |
| Reticulocytes | 0/8 | 10/10 |
| Normoblasts | 0/8 | 4/4 |
| Euchrom. Erythroblasts | 1/32 | 5/5 |
| Polychrom. Erythroblasts | 0/8 | 10/10 |
| Basophilic erythroblasts | 0/8 | 4/4 |
| Proerythroblasts | 0/8 | 4/4 |
| Lymphocytopoiesis | | |
| B lymphocytes | 0/8 | 0/14 |
| Plasma cells | 0/8 | 0/14 |
| T lymphocytes | 0/8 | 0/14 |
| Hepatocytes | 0/8 | 0/4 |
| Kupffer cells | 0/8 | 0/4 |
| Other hepatic cells | 0/8 | 0/8 |

In the following, FIGS. 1 to 4 are described in detail

FIGURES

FIG. 1

Mononuclear cord blood cells were stained with labeled antibodies (anti CD45, anti CD71 and the antibody under investigation, 4B9) and a DNA dye. Antibody binding was measured with a flow cytometer.
  a) This FIG. 1a shows a diagram with the light scatter properties of erythroid precursor cells. For further characterization, the cells characterized by means of their light scatter properties in region R1 were used.
  b) FIG. 1b shows a diagram of fluorescence properties of the cells in region R1 and labeled with CD71-antibody and dye LDS751 labeling all nuclei. Region R2 encloses nucleated cells which express or do not express CD71 antigen.
  c) FIG. 1c shows a diagram of fluorescence properties of the cells in region R2 incubated with CD71 antibodies and CD45 antibodies. The cells in region R3 express CD71 antigen but not CD45 antigen. This diagram demonstrates the differentiation between CD71 positive nucleated erythroid cells (Region R3) and CD45 positive leukocytes.
  d) FIG. 1d shows a diagram of fluorescence properties of the cells in region R2. The cells in region R4 express CD71 antigen and bind to the 4B9 antibody. Thus, antibody 4B9 binds preferentially to CD71 positive cells, which are CD45 negative.

FIG. 2

FIG. 2 discloses absorption of monoclonal antibodies 4B8 and 4B9 with adult erythrocytes, followed by the determination of their binding capability on cord blood cells. It is shown that neither 4B8 antibody nor 4B9 antibody is absorbed by adult red blood cells. For positive and negative controls antibodies against CD71 and glycophorin A were used.

FIG. 3

Flow cytometric investigation of the binding of the monoclonal antibodies 4B8 and 4B9 on cord blood cells and adult blood cells (x-axis: fluorescence intensity).
  a) This histogram shows unstained, negative cord blood cells marked as "unlabeled" and cord blood cells incubated with labeled antibodies 4B8 (marked as 4B8) and 4B9 (marked as 4B9). This demonstrates that cord blood cells are stained by antibodies 4B8 and 4B9.
  b) In this figure, adult blood cells show the same fluorescence intensity (x-axes), whether they are incubated with antibodies 4B8 ("4B8") or 4B9 ("4B9") or with no antibody ("unlabeled"). Thus, antibodies 4B8 and 4B9 do not bind to adult blood cells.

FIG. 4

Immunofluorescent and immunoenzymatic analyses of fetal blood cells.
A) and B) Glycophorin A-positive (marked with "G") fetal erythropoietic cells express the 4B9 antigen (fluorescent, filled black regions in the cells schematically drawn in FIG. 4B). Cell nuclei are stained with DAPI and marked with "B". Obviously, nucleated and enucleated red blood cells are positive for the 4B9 antigen. A1 and B1 show the original fluorescence picture and A2, B2 schematic drawings of A1 and B1 respectively.

The invention claimed is:

1. A method for detecting whether fetal red blood cells or their nucleated precursor cells are present in a sample comprising:
   (a) contacting a sample with a fluorescently labeled antibody that binds to the surface of fetal red blood cells and their nucleated precursor cells, wherein said antibody is not reactive with CD71 or with surface antigens of adult erythroid, lymphatic, or myeloic cells, under conditions in which the antibody binds to fetal red blood cells and their nucleated precursor cells if present in the sample; and
   (b) detecting cells bound by said fluorescently labeled antibody if present in the sample, wherein binding of the antibody indicates that the cell is a fetal red blood cell or a nucleated precursor cell thereof.

2. The method according to claim 1, wherein fetal red blood cells or their nucleated precursor cells are present in the sample and wherein step (b) comprises detecting cells bound by said fluorescently labeled antibody.

3. The method according to claim 2, further comprising analyzing cells bound by said fluorescently labeled antibody for a chromosomal or genetic defect.

4. The method according to claim 3, wherein the antibody is a monoclonal antibody.

5. The method according to claim 4, wherein the sample is maternal blood.

6. The method according to claim 3, wherein the sample is maternal blood.

7. The method according to claim 2, wherein the antibody is a monoclonal antibody.

8. The method according to claim 7, wherein the sample is maternal blood.

9. The method according to claim 2, wherein the sample is maternal blood.

10. The method according to claim 1, which comprises separating cells bound by said fluorescently labeled antibody by flow cytometry, solid phase separation, immunomagnetic bead separation, or panning on plastic surfaces.

11. The method according to claim 10, wherein the antibody is a monoclonal antibody.

12. The method according to claim 11, wherein the sample is maternal blood.

13. The method according to claim 10, wherein the sample is maternal blood.

14. The method according to claim 1, wherein the antibody is a monoclonal antibody.

15. The method according to claim 14, wherein the sample is maternal blood.

16. The method according to claim 1, wherein the sample is maternal blood.

* * * * *